United States Patent
Matsumoto (10) Patent No.: US 7,038,788 B2
(45) Date of Patent: May 2, 2006

(54) ANGLE-OF-ROTATION MEASURING DEVICE AND ANGLE-OF-ROTATION MEASURING METHOD

(75) Inventor: Kenji Matsumoto, Tokyo (JP)

(73) Assignee: Citizen Watch Co., Ltd., Tokyo (JP)

( * ) Notice: Subject to any disclaimer, the term of this patent is extended or adjusted under 35 U.S.C. 154(b) by 290 days.

(21) Appl. No.: 10/472,250

(22) PCT Filed: Feb. 21, 2002

(86) PCT No.: PCT/JP02/01572

§ 371 (c)(1),
(2), (4) Date: Sep. 22, 2003

(87) PCT Pub. No.: WO02/077617

PCT Pub. Date: Oct. 3, 2002

(65) Prior Publication Data

US 2004/0119982 A1    Jun. 24, 2004

(30) Foreign Application Priority Data

Mar. 22, 2001 (JP) .............................. 2001-081991

(51) Int. Cl.
*G01B 9/02* (2006.01)
(52) U.S. Cl. ..................................... 356/484; 356/487
(58) Field of Classification Search ................ 356/487, 356/488, 491, 494
See application file for complete search history.

(56) References Cited

U.S. PATENT DOCUMENTS 5,229,834 A * 7/1993 Lequime ..................... 356/365
6,327,037 B1 * 12/2001 Chou et al. .................. 356/484

FOREIGN PATENT DOCUMENTS

| JP | 51-51254 | 12/1976 |
| JP | 57-53642 | 3/1982 |
| JP | 57-101705 | 6/1982 |
| JP | 2-183142 | 7/1990 |
| JP | 6-147984 | 5/1994 |

* cited by examiner

*Primary Examiner*—Gregory Toatley
*Assistant Examiner*—Marissa J Detschel
(74) *Attorney, Agent, or Firm*—Finnegan, Henderson, Farabow, Garrett and Dunner, L.L.P.

(57) ABSTRACT

The invention is directed to the provision of a device and method for measurement of angle of rotation for measuring in a non-contacting fashion the concentration of an optically active substance such as a sugar, amino acid, vitamin, or the like dissolved in a sample. According to the invention, A coherent beam is split into two beams, one being an object beam and the other being a reference beam, the object beam passed through the sample is converted by a quarter wave plate into mutually perpendicular polarization components having therebetween a phase difference proportional to the angle of rotation produced by the sample, and the angle of rotation produced by the sample is obtained from the phase difference occurring between beat signals produced by causing the object beam with the reference beam. Alternatively, a coherent beam is directed into the sample, the beam passed through the sample is converted by a quarter wave plate into mutually perpendicular polarization components having therebetween a phase difference proportional to the angle of rotation produced by the sample, and the angle of rotation produced by the sample is measured based on the phase of a beat signal produced by causing the mutually perpendicular polarization components to interfere with each other by means of a polarizer.

12 Claims, 3 Drawing Sheets

ANGLE-OF-ROTATION MEASURING DEVICE AND ANGLE-OF-ROTATION MEASURING METHOD

TECHNICAL FIELD

The present invention relates to a device, for measurement of angle of rotation, for measuring in a non-contacting fashion the concentration of an optically active substance such as a sugar, amino acid, vitamin, or the like dissolved in a sample and, more particularly, to a device for high-sensitivity measurement of angle of rotation for noninvasively measuring the concentration of blood sugar in a living body.

BACKGROUND ART

Conventionally, to determine the angle of optical rotation, i.e., the angle through which the plane of polarization is rotated in a sample, linearly polarized light is directed into the sample and the beam of light passed through the sample is input via an analyzer to a photodiode for conversion into an electrical signal. The angle of rotation is determined from the thus obtained signal. When the tilt angle of the transmission axis of the analyzer with respect to the transmission axis of a polarizer is denoted by $\theta$, and the angle of rotation produced by the sample is denoted by $\alpha$, the intensity of light, I, received by the photodiode is given as $I = T \times I_0 \cos(\theta - \alpha)^2$. Here, T represents the transmittance considering all attenuations due to reflections and absorptions in the sample, the polarizer, and the analyzer, and $I_0$ designates the intensity of the incident light. As can be seen from the above equation, as the analyzer is rotated, a minimum point is obtained for every rotation angle $\pi$ (rad). The angle of optical rotation can be obtained from the angle of the analyzer at this minimum point. For increased accuracy and sensitivity, a polarization plane vibration method is generally used.

Figure 5:
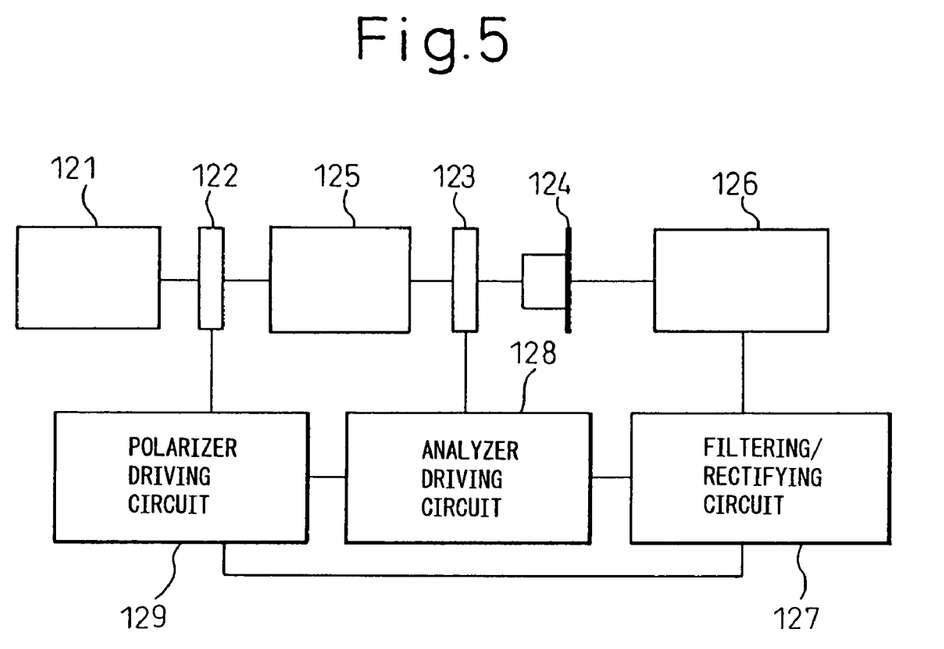
FIG. 5 is a diagram showing an example of a device for measurement of angle of rotation according to the prior art.

This will be explained below with reference to FIG. 5. Monochromatic light emitted from a light source 121 enters a polarizer 122 which is driven by a polarizer driving circuit 129 and vibrating with a frequency f and an angular amplitude $\theta$, and the light is converted into linearly polarized light whose plane of polarization is vibrating in a rotating fashion. When this beam of light is introduced into a sample 125 and passed through an analyzer, a signal of frequency f is obtained from a photodiode 124. Assume here that the plane of polarization is rotated through a by the optical activity of the sample 125; then, when the polarizer 122 and the analyzer 123 are arranged at right angles to each other, a signal with an inverted phase is obtained, depending on whether the optical activity of the sample 125 is right-handed or left-handed. The signal obtained from the photodiode 124 is amplified by an amplifier circuit 126 and filtered and rectified by a filtering/rectifying circuit 127 to obtain the phase. Then, the angle of the analyzer is determined in accordance with the optical null method by rotating the polarizer 123 by means of an analyzer driving circuit 128 in the normal or reverse direction according to the obtained phase so that the amount of light transmission becomes a minimum. A signal of double frequency 2f is obtained at an equilibrium point, but the 2f component is removed by synchronous detection. The angle of the analyzer at the equilibrium point corresponds to the angle of optical rotation produced by the sample. As a method of rotating the plane of polarization, the polarizer is mechanically rotated, or alternatively, a Faraday rotator is used.

The above method, however, requires that the polarization state of light be preserved to a certain extent by transmission through the sample, and therefore it can only measure transparent or near-transparent samples. The resulting disadvantage is that, in the case of a sample such as a scattering sample, that changes the polarization state to random polarization, the S/N ratio degrades and the angle of optical rotation cannot be measured. Another disadvantage is that, as the polarizer must be mechanically rotated, or a Faraday rotator must be used, to rotate the plane of polarization, the device becomes complex and the price and size increase.

DISCLOSURE OF THE INVENTION

According to the present invention, there is provided a device, for measurement of angle of rotation, comprising: a coherent light source; beam splitting means for splitting a beam from the light source into two beams, one being an object beam and the other being a reference beam; frequency modulating means for introducing a slight frequency difference between the two beams; a quarter wave plate, disposed in a light path of the object beam, for converting the angle of rotation produced by a sample into a phase difference between mutually perpendicular linearly polarized beams after passage through the sample; beam combining means for combining the object beam with the reference beam; polarization splitting means for splitting interference light occurring between the object beam and the reference beam into two phase interference signals according to polarization directions; and optical-to-electrical converting means for converting the interference signals into electrical signals.

The beam splitting means and the frequency modulating means may each be constructed from a diffraction grating whose pitch is approximately equal to the wavelength of the beam.

According to the present invention, there is also provided a device for measurement of angle of rotation, comprising: a coherent light source; a quarter wave plate for converting the angle of rotation produced by a sample into a phase difference between mutually perpendicular polarization components after passage through the sample; frequency modulating means for frequency-modulating one of the polarization components; a polarizer for obtaining an interference signal between the mutually perpendicular polarization components; and optical-to-electrical converting means for converting the interference signal into an electrical signal.

According to the present invention, there is also provided a device for measurement of angle of rotation, comprising: a coherent light source; frequency modulating means for frequency-modulating a polarization component contained in a beam from the light source and polarized in one specific direction; a beam splitting means for splitting the beam into two beams; a quarter wave plate for converting one of the two beams into right-circularly polarized light and left-circularly polarized light depending on the polarization components of the one beam; a quarter wave plate for converting the angle of rotation produced by a sample into a phase difference between mutually perpendicular linearly polarized beams after passage through the sample; a first polarizer for obtaining an interference signal between the mutually perpendicular linearly polarized beams; a first optical-to-electrical converting element for converting the interference signal into an electrical signal; a second polarizer for obtaining an interference signal between polarization components of the other one of the two beams; and a second optical-to-electrical converting element for converting the interference signal into an electrical signal.

The frequency modulating means may make use of a phase modulating means constructed from a liquid crystal device.

The device of the present invention may further include a phase correcting element for applying a phase correction to one of the two beams being caused to interfere with each other in order to obtain a beat signal having a phase difference proportional to the angle of rotation produced by the sample, wherein feedback is applied to a phase correction amount so that an output produced by phase-detecting the beat signal becomes a maximum or a minimum, and the angle of rotation is detected from the phase correction amount.

The device of the present invention may further include a phase correcting element for applying a phase correction to one of the two beams being caused to interfere with each other in order to obtain a beat signal having a phase difference proportional to the angle of rotation produced by the sample, wherein feedback is applied to a phase correction amount so that an output produced by phase-detecting the beat signal becomes a maximum or a minimum, and the angle of rotation is detected from the phase correction amount.

The phase correcting element may be constructed from a liquid crystal device.

According to a method for measurement of angle of rotation of the present invention, a coherent beam is split into two beams, one being an object beam and the other being a reference beam, the object beam, after passage through a sample, is converted by a quarter wave plate into mutually perpendicular polarization components having therebetween a phase difference proportional to the angle of rotation produced by the sample, and is caused to interfere with the reference beam having a slight frequency difference relative to the object beam, and the angle of rotation produced by the sample is measured based on a phase difference occurring between two beat signals resulting from the interference.

Further, according to a method for measurement of angle of rotation of the present invention, a coherent beam is directed into a sample, the beam, after passage through the sample, is converted by a quarter wave plate into mutually perpendicular polarization components having therebetween a phase difference proportional to the angle of rotation produced by the sample, a slight frequency difference is introduced between the polarization components, the polarization components are caused to interfere with each other by means of a polarizer, and the angle of rotation produced by the sample is measured based on the phase of a beat signal resulting from the interference.

According to the present invention, not only in the case of a transparent sample, but in the case of a sample such as a scattering sample that does not preserve the state of polarization, the angle of optical rotation can be measured by improving the S/N ratio. Furthermore, as there is no need to rotate the plane of polarization by rotating the polarizer or by using a Faraday rotator, the device can be simplified in construction, and reductions in size and cost can thus be achieved.

Further, as the interferometer is a complete common-path interferometer, there is no need for highly precise alignment of the optical axis, and the stability is also extremely high, so that the angle of optical rotation can be measured with high sensitivity.

When a liquid crystal device is used as the frequency modulating means, the need for frequency modulation by mechanical vibrations of a mirror or by an acousto-optic modulator can be eliminated; as a result, the device can be simplified in construction, achieving reductions in size and cost.

Furthermore, by applying a phase correction to the liquid crystal device and feeding it back to the liquid crystal device driving signal so that the phase detection signal becomes a maximum or a minimum, effects due to fluctuations in the intensity of the light source or variations in the transmittance of the sample can be canceled, and thus the angle of rotation produced by the sample can be detected with high accuracy.

Other features and advantages of the present invention will be understood from the detailed description of the invention given below.

DETAILED DESCRIPTION OF THE INVENTION

The method for measurement of angle of rotation of the present invention utilizes the fact that the phenomenon of optical rotation occurs due to the difference between the refractive indices of right-circularly polarized light and left-circularly polarized light. According to the method of the present invention, the phase difference arising from the difference in refractive index between the two circularly polarized beams is detected by converting it into light intensity by causing the two beams to interfere with two different reference beams, or by causing the two circularly polarized beams to interfere with each other.

First, an outline will be given of the method in which the phase difference caused by the difference in refractive index between the two circularly polarized beams is detected by converting it into light intensity by causing the two beams to interfere with two different reference beams.

For example, if linearly polarized light entering a sample is regarded as a superposition of right- and left-circularly polarized beams, the electric field components of the right- and left-circularly polarized light beams are respectively expressed as $E_y = A \cos(\omega t + \delta_0)$ $E_x = A \cos(\omega t + \delta_0 - \pi/2)$ and $E_y = A \cos(\omega t + \delta_0)$ $E_x = A \cos(\omega t + \delta_0 + \pi/2)$ When the linearly polarized light (oriented 45° with respect to the Y axis) enters the sample, phase differences ±θ are respectively added to the right- and left-circularly polarized light components by the optical activity of the sample, and the components are respectively expressed as $E_y = A \cos(\omega t + \delta_0 + \theta)$ $E_x = A \cos(\omega t + \delta_0 - \pi/2 + \theta)$ and $E_y = A \cos(\omega t + \delta_0 - \theta)$ $E_x = A \cos(\omega t + \delta_0 + \pi/2 - \theta)$ When the components are passed through a quarter wave plate whose fast axis is oriented so as to coincide with the X axis, the phase along the X axis advances by $\pi/2$ with respect to the Y axis, and hence the components are respectively expressed as $E_y = A \cos(\omega t + \delta_0 + \theta)$ $E_x = A \cos(\omega t + \delta_0 + \theta)$ and $E_y = A \cos(\omega t + \delta_0 - \theta)$ $E_x = A \cos(\omega t + \delta_0 - \theta)$ The components are thus converted into mutually perpendicular linearly polarized beams oriented 45° with respect to the X axis and the Y axis, respectively. When the two beams are separated using a polarization beam splitter or a combination of a beam splitter and a polarizer, and are caused to interfere with frequency modulated reference beams propagated through a different light path, the resulting beat signals are $A \cos(\Delta \omega t + \delta_0 + \theta)$ $A \cos(\Delta \omega t + \delta_0 - \theta)$ Thus, the beat signals phase-modulated by the optical activity of the sample are obtained.

Here, when a beat signal frequency is known, a beat signal phase can be detected with good sensitivity by synchronous detection. That is, the beat signal $A \cos(\Delta \omega t + \delta_0 + \theta)$ is multiplied by a sinusoidal signal $\sin(\Delta \omega t + \delta_0)$ of the same frequency, to obtain $A(\sin(2\Delta \omega t + 2\delta_0 + \theta) + \sin(\theta))/2$ When only the DC component is extracted by a low-pass filter, the result is $A \sin(\theta)/2$ and the phase θ can thus be determined. This means frequency-modulating the beat signal frequency $\Delta \omega$ into DC and $2\Delta \omega$ (double frequency) by multiplying with the signal of the same frequency, and means that a band-pass filter having a center frequency equal to the signal frequency can be replaced by the extraction of the DC component using a low-pass filter. This, as a result, achieves a narrow band-pass filter, and the S/N ratio can be improved. In this way, the angle of rotation can be obtained with good sensitivity even in the case of a test sample such as a scattering object.

Next, an outline will be given of the method in which the phase difference is detected by converting it into light intensity by causing the two circularly polarized beams to interfere with each other.

For example, if it is assumed that a phase difference of ±θ occurs between the two circularly polarized beams because of the optical activity of the sample while the light is passing through the sample, the right- and left-circularly polarized light components are respectively expresses as $E_y = A \cos(\omega t + \delta_0 + \theta)$ $E_x = A \cos(\omega t + \delta_0 - \pi/2 + \theta)$ and $E_y = A \cos(\omega t + \delta_0 - \theta)$ $E_x = A \cos(\omega t + \delta_0 + \pi/2 - \theta)$ Their superposition is given as $E_y = 2A \cos(\omega t + \delta_0) \cos(\theta)$ $E_x = 2A \cos(\omega t + \delta_0) \sin(\theta)$ Here, $E_y = 1/\tan(\theta) E_x$, and the result is a linearly polarized beam with a tilt θ. That is, the phase difference 2θ between the circularly polarized beams results in the angle of rotation of θ. Accordingly, the phase θ due to the optical rotation can be detected by converting it to light intensity by causing the right- and left-circularly polarized beams to interfere with each other.

Further, if a slight frequency difference $\Delta \omega$ (several kilohertz to several megahertz) is given between the two interfering beams whose electric fields are respectively $E1 = A \cos((\omega + \Delta \omega)t + \delta_0)$ $E2 = A \cos(\omega t + \delta_1)$ then the interference light intensity I is given as $I = |E_1 + E_2|^2 = A^2 \cos^2((\omega + \Delta \omega)t + \delta_0) + A^2 \cos^2(\omega t + \delta_1) + 2A^2 \cos^2((\omega + \Delta \omega)t + \delta_0) \cos(\omega t + \delta_1)$ Since the optical-to-electrical converter cannot respond to light frequency, the light intensity is $I = I_0 + A^2 \cos(\Delta \omega t + \delta)$ which is the sum of the DC component and the beat signal.

One method for slightly shifting the light frequency is to use an acousto-optic modulator (AOM), in which case the frequency to be shifted is determined by the ultrasound frequency supplied to the AOM. For example, when the two light beams are frequency-modulated with 100 MHz and 101 MHz, respectively, a beat signal of 1 MHz is obtained, making electrical signal processing possible.

The reason that the two light beams are frequency-modulated is to cancel frequency variations of the light source, but it will be appreciated that a beat signal can also be obtained if only one of the light beams is frequency-modulated.

When the beam diameter of the two interfering beams is made substantially equal to the size of the light receiving area of the optical-to-electrical converter, beams deflected by refraction, diffraction, or scattering do not overlap with the reference light on the optical-to-electrical converter, and therefore, do not contribute to the interference. Further, multiple scattering beams incident on the optical-to-electrical converter are random both in wavefront and in polarization plane, and coherence is not preserved; therefore, such beams also do not contribute to the interference. As a result, only the light components that have traveled in straight lines through the sample interfere, producing a beat signal. If a signal of a known beat frequency is acquired by filtering, the angle of rotation produced by a scattering object can also be measured.

The preferred embodiments of the present invention will be described below with reference to drawings.

Figure 1:
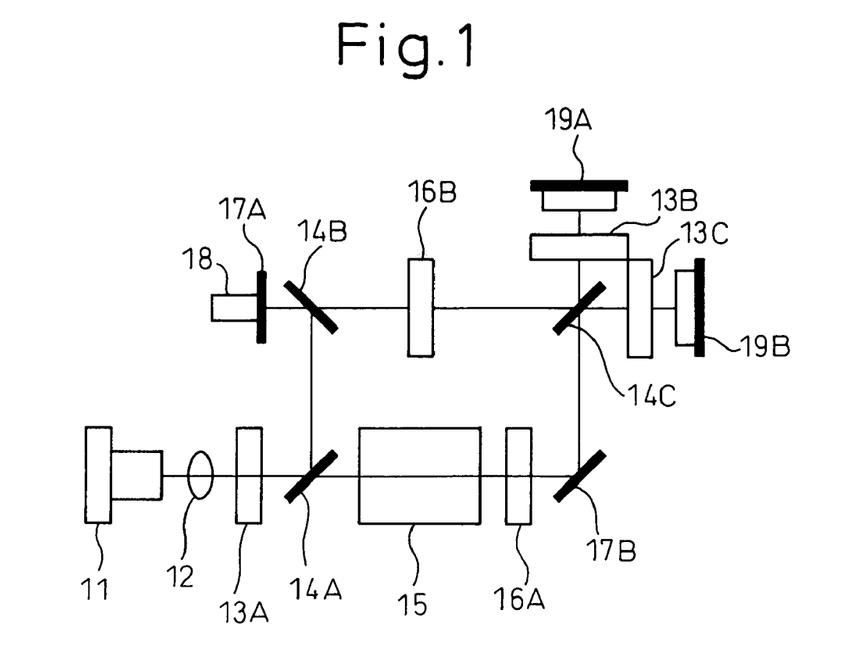
FIG. 1 is a diagram showing an optical system of a device for measurement of angle of rotation according to a first embodiment of the present invention.

FIG. 1 shows an optical system according to a first embodiment. A beam of light emitted from a laser diode 11 is collimated by a lens 12 into a beam of parallel light, which is converted by a polarizer 13A into linearly polarized light vibrating in vertical direction. The light is then separated into two beams by a half-silvered mirror 14A. The light transmitted therethrough enters a test sample 15 where a phase difference of ±θ occurs between right-circularly polarized light and left-circularly polarized light because of the optical activity of the sample. Next, by passing through a quarter wave plate 16A whose fast axis coincides with the horizontal or vertical axis, the right- and left-circularly polarized beams are converted into mutually perpendicular linearly polarized beams each oriented 45° with respect to the vertical axis.

On the other hand, the beam reflected by the half-silvered mirror 14A is reflected toward a mirror 17A by another half-silvered mirror 14B. The mirror 17A is supported on an electrostrictive element 18 such as a PZT; periodic vibrations are applied in the optical axis direction by applying a periodic signal to the electrostrictive element. For example, suppose that a sawtooth wave signal whose amplitude is an n multiple of the wavelength (n=1, 2, 3, . . . ) is applied to the electrostrictive element, causing the mirror 17A to move at speed v; then, a frequency modulation of $\Delta f/f = v/(c+v)$ is obtained, and a beat signal is produced by the interference between the two beams.

For the frequency modulation method, other techniques can also be used, such as the frequency modulation using an acousto-optic modulator (AOM) or the frequency modulation through control of the drive current of the laser diode.

The frequency-modulated beam is passed through a quarter wave plate 16B whose optical axis is oriented in the same direction as that of the quarter wave plate 16A. Then, the beams are combined by a half-silvered mirror 14C, and the beam passed through the sample and the component of the reference beam polarized in the same direction are caused to interfere with each other by polarizers 13B and 13C whose transmission axes are oriented 45° with respect to the vertical axis and at right angles to each other. As a result, two-phase sinusoidal signals having a phase difference proportional to the angle of rotation produced by the sample are obtained, and these signals are converted by photodiodes 19A and 19B into electrical signals.

For example, consider a sugar solution of concentration 10 g/dl as the test sample; here, if the specific rotation of the sugar is 66.5°, and optical pathlength is 10 mm, then the angle of rotation, α, the light undergoes by passing through the sample is given as α=0.665° from the following equation.

α=l[dm]×C [g/dl]×66.5/100 (l: optical pathlength, C: concentration)=0.1×10×66.5/100=0.665

Hence, the phase difference θ between the two phase signals is θ=2α=2×0.665×π/180=0.023 [rad].

In principle, the phase difference can be obtained using the above-described synchronous detection technique by multiplying together the two phase signals obtained from the photodiodes 19A and 19B and by low-pass filtering the result to extract the DC component. Further, by applying digital signal processing techniques such as A/D converting the two phase signals and digitally multiplying the high-accuracy sinusoidal waves, a more accurate phase measurement can be achieved, and the concentration of an optically active substance can be obtained with high accuracy.

Figure 2:
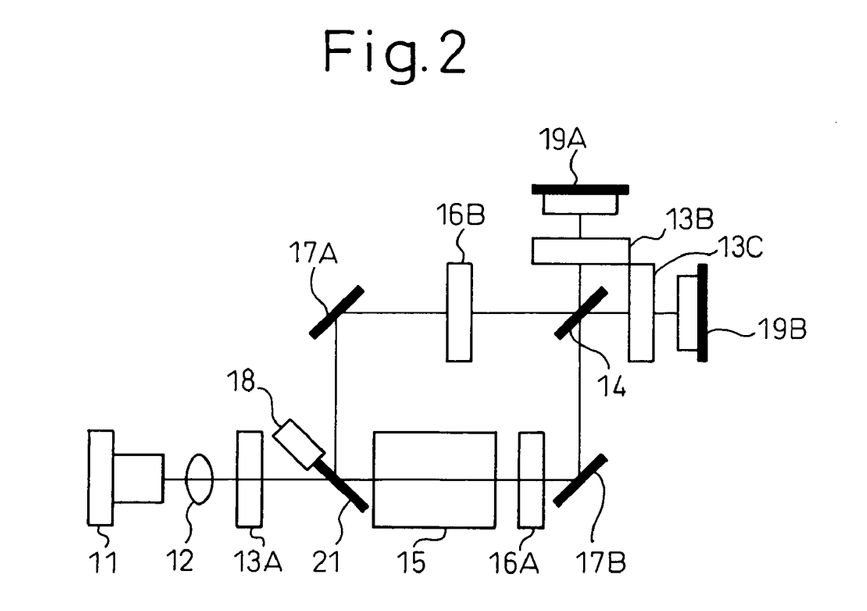
FIG. 2 is a diagram showing an optical system of a device for measurement of angle of rotation according to a second embodiment of the present invention.

FIG. 2 shows an optical system according to a second embodiment. A beam of light emitted from a laser diode 11 is collimated by a lens 12 into a beam of parallel light, which is converted by a polarizer 13A into linearly polarized light vibrating in vertical direction. The light is then separated by a diffraction grating 21 into two beams of light, i.e., diffracted light and light transmitted in straight lines therethrough. The diffraction grating 21 is supported on an electrostrictive element 18 such as a PZT; periodic vibrations are applied in a direction perpendicular to the grating by applying a periodic signal to the electrostrictive element.

The light transmitted in straight lines through the diffraction grating 21 enters a test sample 15 where a phase difference of ±θ occurs between right-circularly polarized light and left-circularly polarized light because of the optical activity of the sample. Next, by passing through a quarter wave plate 16A whose fast axis coincides with the horizontal or vertical axis, the right- and left-circularly polarized beams are converted into mutually perpendicular linearly polarized beams each oriented 45° with respect to the vertical axis.

On the other hand, a phase term 2πx/D (x: displacement of diffraction grating, D: pitch of diffraction grating), which depends on the position of the diffraction grating 21, is superimposed on the first-order diffracted light diffracted by the diffraction grating 21; here, the phase term with a positive or negative sign is superimposed, depending on the direction of diffraction. Accordingly, the respective diffracted light beams are simply expressed as $E_1 = A \cos(\omega t + 2\pi x/D)$ $E_2 = A \cos(\omega t - 2\pi x/D)$ Here, the instantaneous angular frequency $\omega_1$ of the +1st-order diffracted light $E = A \cos(\omega t + 2\pi x/D)$ is given as $\omega_1 = d/dt(\omega t + (2\pi/D)\int v(t)dt) = \omega + 2\pi v(t)/D$ (v(t): moving speed of diffraction grating) Accordingly, frequency modulation proportional to the speed of the diffraction grating can be performed, and the difference in angular frequency from the 0th-order light is 2πv(t)/D. That is, there is no substantial difference between phase modulation and frequency modulation. When the speed v is constant, the intensity of the interference light of the 0th-order diffracted light and 1st-order diffracted light changes in sinusoidal fashion, and a beat signal of a constant cycle can be obtained.

As the beam splitting function and the frequency modulating function, which were implemented separately in the first embodiment, can both be implemented by the diffraction grating 21, as described above, the optical system can be simplified in construction, and reductions in size and cost can thus be achieved.

The beam frequency-modulated by the diffraction grating 21 is passed through a quarter wave plate 16B whose optical axis is oriented in the same direction as that of the quarter wave plate 16A; then, the beams are combined by a half-silvered mirror 14, and the same polarization components are caused to interfere with each other by polarizers 13B and 13C. As a result, two-phase sinusoidal signals having a phase difference proportional to the angle of rotation produced by the sample are obtained, and thus the angle of rotation can be determined, as in the first embodiment.

Figure 3:
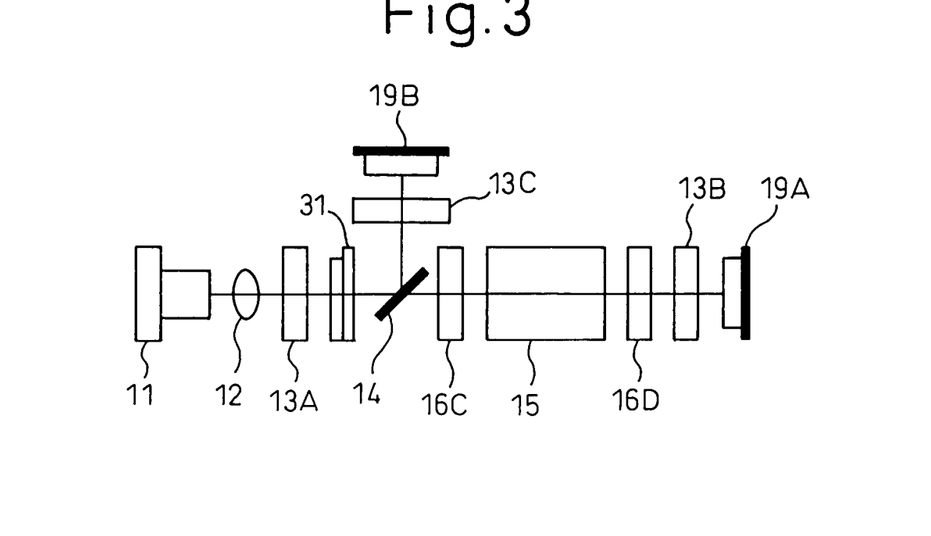
FIG. 3 is a diagram showing an optical system of a device for measurement of angle of rotation according to a third embodiment of the present invention.

FIG. 3 shows an optical system according to a third embodiment. A beam of light emitted from a laser diode 11 is collimated by a lens 12 into a beam of parallel light, which is converted by a polarizer 13A into linearly polarized light vibrating in a direction tilted 45° with respect to the vertical direction. Next, the polarization component in either the horizontal or the vertical direction is phase-modulated by a liquid crystal device 31. The liquid crystal device 31 is a liquid crystal device of homogeneous alignment in which the long axes of the liquid crystal molecules are aligned in the horizontal or vertical direction. When a voltage is applied to the liquid crystal device 31, the liquid crystal molecules stand up, and the refractive index in the molecular long axis direction changes; phase modulation can thus be achieved.

As shown in the second embodiment, there is no substantial difference between phase modulation and frequency modulation. When phase modulation is applied to only one of the polarization components by the liquid crystal device, as described above, a beat signal can be obtained by causing the mutually perpendicular polarization components to interfere with each other.

Next, the light is separated by a half-silvered mirror 14 into reflected light and transmitted light, and the transmitted light enters a quarter wave plate 16C whose fast axis is oriented 45° with respect to the horizontal axis; here, the components vibrating in the horizontal and vertical directions respectively can be converted into counter-rotating circularly polarized light components. Next, the circularly polarized light components enter the test sample 15 where a phase difference of ±θ is introduced between the right-circularly polarized light and the left-circularly polarized light because of the optical activity of the sample. Next, by passing through a quarter wave plate 16D whose optical axis coincides with, or is oriented at right angles to, that of the quarter wave plate 16C, the right- and left-circularly polarized light components are converted into mutually perpendicular polarization components each vibrating in the horizontal or vertical direction.

When these components are passed through a polarizer 13B whose transmission axis is oriented 45° with respect to the horizontal or vertical direction, an interference signal between the mutually perpendicular polarization components is obtained. As one of the components is phase-modulated, a beat signal is produced, and this beat signal is converted by a photodiode 19A into an electrical signal.

Here, the two interfering beams are the mutually perpendicular polarization components of a single beam. Accordingly, as the interferometer is a complete common-path interferometer, there is no need for a highly precise alignment of the optical axis as in two-beam interference, and the stability of the interferometer is also high.

On the other hand, the beam reflected by the half-silvered mirror 14 enters a polarizer 13C oriented in the same manner as the polarizer 13B; here also, an interference signal between the mutually perpendicular polarization components is obtained. As one of the components is phase-modulated, a beat signal is obtained through optical-to-electrical conversion by a photodiode 19B.

The beat signal obtained from the photodiode 19B is independent of the optical activity of the sample, and the angle of rotation produced by the sample can be determined from the phase difference between the signals obtained from the photodiodes 19A and 19B. Furthermore, as effects other than the optical activity of the sample, such as fluctuations in the intensity of the light source and variations in the response of the liquid crystal device, are canceled, the angle of rotation produced by the sample can be detected with high sensitivity.

Figure 4:
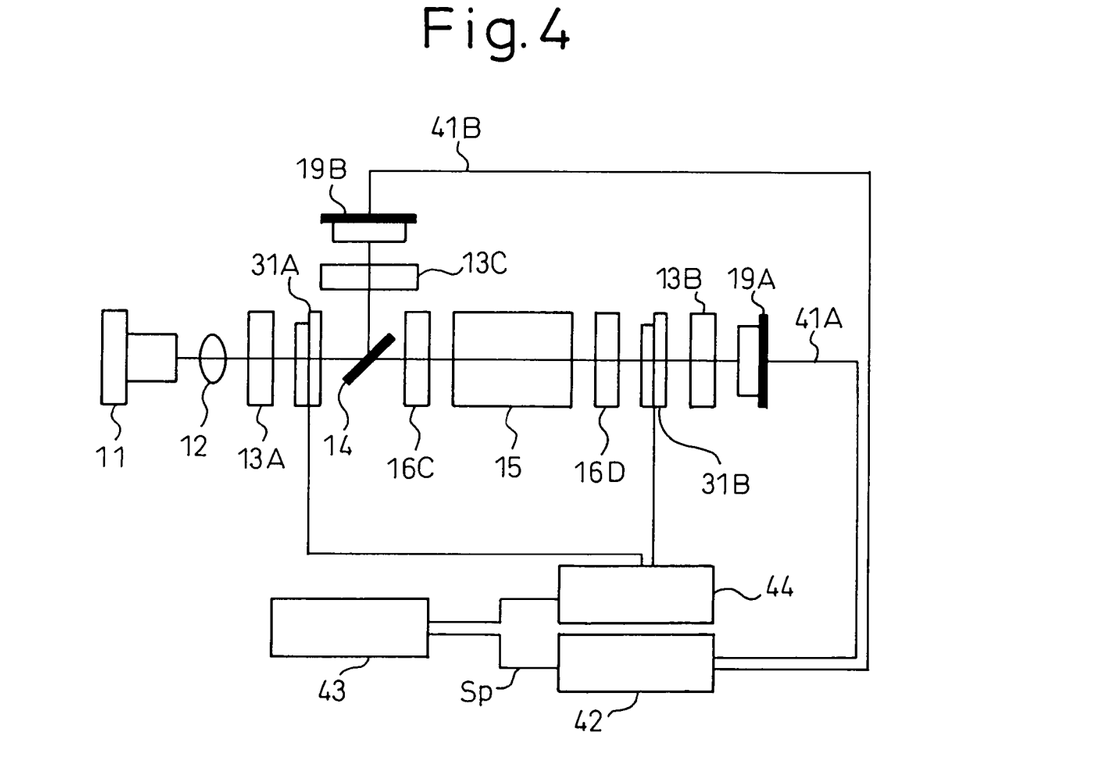
FIG. 4 is a diagram showing an optical system of a device for measurement of angle of rotation according to a fourth embodiment of the present invention.

FIG. 4 shows an optical system according to a fourth embodiment. The feature of this embodiment is that a phase correction is applied by means of a liquid crystal device 31B; otherwise, the optical system is the same as that of the third embodiment. The following description is given with reference to FIG. 4 in which the liquid crystal device 31B is added in the configuration of the third embodiment, but it will be recognized that a similar effect can be obtained if the phase correction by the liquid crystal device 31B is applied in the first or second embodiment.

A beam of light emitted from a laser diode 11 is collimated by a lens 12 into a beam of parallel light, which is converted by a polarizer 13A into linearly polarized light vibrating in a direction tilted 45° with respect to the vertical direction. Next, the polarization component in either the horizontal or the vertical direction is phase-modulated by a liquid crystal device 31A. The liquid crystal device 31A is a liquid crystal device of homogeneous alignment in which the long axes of the liquid crystal molecules are aligned in the horizontal or vertical direction. When a voltage is applied to the liquid crystal device, the liquid crystal molecules stand up, and the refractive index in the molecular long axis direction changes; phase modulation can thus be achieved.

As shown in the second embodiment, there is no substantial difference between phase modulation and frequency modulation. When phase modulation is applied to only either one of the polarization components by the liquid crystal device as described above, a beat signal can be obtained by causing the mutually perpendicular polarization components to interfere with each other.

The light is separated by a half-silvered mirror 14 into reflected light and transmitted light, and the transmitted light enters a quarter wave plate 16C whose slow axis is oriented 45° with respect to the horizontal axis; here, the components vibrating in the horizontal and vertical directions respectively can be converted into counter-rotating circularly polarized light components. Next, the light components enter the test sample 15, and a phase difference of ±θ occurs between the right-circularly polarized light and the left-circularly polarized light because of the optical activity of the sample. Next, by passing through a quarter wave plate 16D whose optical axis coincides with, or is oriented at right angles to, that of the quarter wave plate 16C, the right- and left-circularly polarized light components are converted into mutually perpendicular polarization components each vibrating in the horizontal or vertical direction.

When these components are passed through a polarizer 13B whose transmission axis is oriented 45° with respect to the horizontal or vertical direction, an interference signal between the mutually perpendicular polarization components is obtained. As one of the components is phase-modulated, a beat signal 41A is obtained from a photodiode 19A.

The beam undergoes a phase correction in the liquid crystal device 31B. In the liquid crystal device 31B, the long axes of the liquid crystal molecules are aligned in the horizontal or vertical direction; therefore, by adjusting the amount of phase correction by varying the liquid crystal driving signal, the phase of the beat signal 41A can be set as desired.

On the other hand, the beam reflected by the half-silvered mirror 14 enters a polarizer 13C oriented in the same manner as the polarizer 13B; here, also, an interference signal between the mutually perpendicular polarization components is obtained. As one of the components is phase-modulated, a beat signal 41B is obtained from a photodiode 19B.

Here, the beat signals 41A and 41B are respectively expressed as $$E_A = A\cos(\Delta\omega t + 2\theta + \phi + \delta_0)$$

$$E_B = A\cos(\Delta\omega t + \delta_0)$$

(where $\Delta\omega$: beat signal angular frequency, $\theta$: angle of optical rotation (rad), $\phi$: amount of phase correction applied by liquid crystal device 31B, $\delta_0$: initial phase) The beat signals are multiplied together in an amplifier/phase detector circuit 42, and a phase detection signal Sp is obtained by extracting the DC component using a low-pass filter.

That is, from the equation $$E_A \times E_B = A^2\cos(\Delta\omega t + 2\theta + \phi + \delta_0)\cos(\Delta\omega t + \delta_0) = A^2/2\{\cos(2\Delta\omega t + 2\theta + \phi + 2\delta_0) + \cos(2\theta + \phi)\}$$

Sp=$A^2/2 \cdot \cos(2\theta + \phi)$ is obtained, that is, the phase detection signal Sp is a sinusoidal wave having the angle of rotation, $\theta$, and the phase term, $\phi$, contributed by the liquid crystal device 31B.

Here, the liquid crystal driving voltage is controlled by a digital signal processing circuit 43 so as to maintain Sp at a constant value Sp1, and the liquid crystal device 31B is controlled in a closed loop via a liquid crystal driving circuit 44.

Alternatively, the amplifier/phase detector circuit 42 may be configured to perform only signal amplification, and the phase detection signal Sp may be obtained through digital processing in the digital signal processing circuit 43 by synchronizing it to the signal generated to drive the liquid crystal device 31A.

The driving voltage to the liquid crystal device 31B changes with the angle of rotation produced by the sample 15, and the angle of rotation can thus be detected.

By applying feedback to the liquid crystal driving signal so that the value of Sp1 becomes a maximum or a minimum, effects due to fluctuations in the intensity of the light source or variations in the transmittance of the sample can be canceled, and thus the angle of rotation produced by the sample can be detected with high accuracy.

What is claimed is:

1. A device for measurement of angle of rotation, comprising: a coherent light source; beam splitting means for splitting a beam from said light source into two beams, one being an object beam and the other being a reference beam; frequency modulating means for introducing a slight frequency difference between said two beams; a quarter wave plate, disposed in a light path of said object beam, for converting the angle of rotation produced by a sample into a phase difference between mutually perpendicular linearly polarized beams after passage through said sample; beam combining means for combining said object beam with said reference beam; polarization splitting means for splitting interference light occurring between said object beam and said reference beam into two phase interference signals according to polarization directions; and optical-to-electrical converting means for converting said interference signals into electrical signals.

2. A device for measurement of angle of rotation as claimed in claim 1, wherein said beam splitting means and said frequency modulating means are each constructed from a diffraction grating whose pitch is approximately equal to the wavelength of said beam.

3. A device for measurement of angle of rotation, comprising: a coherent light source; frequency modulating means for frequency-modulating a polarization component contained in a beam from said light source and polarized in one specific direction; a beam splitting means for splitting said beam into two beams; a quarter wave plate for converting one of said two beams into right-circularly polarized light and left-circularly polarized light depending on the polaraization components of said one beam; a quarter wave plate for converting the angle of rotation produced by a sample into a phase difference between mutually perpendicular linearly polarized beams after passage through said sample; a first polarizer for obtaining an interference signal between said mutually perpendicular linearly polarized beams; a first optical-to-electrical converting element for converting said interference signal into an electrical signal; a second polarizer for obtaining an interference signal between polarization components of the other one of said two beams; and a second optical-to-electrical converting element for converting said interference signal into an electrical signal.

4. A device for measurement of angle of rotation as claimed in claim 1 or 3, wherein said frequency modulating means makes use of a phase modulating means constructed from a liquid crystal device.

5. A device for measurement of angle of rotation as claimed in claim 1 or 2, further comprising a phase correcting element for applying a phase correction to one of said two beams being caused to interfere with each other in order to obtain a beat signal having a phase difference proportional to the angle of rotation produced by said sample, wherein feedback is applied to a phase correction amount so that an output produced by phase-detecting said beat signal becomes a maximum or a minimum, and the angle of rotation is detected from said phase correction amount.

6. A device for measurement of angle of rotation as claimed in claim 3, further comprising a phase correcting element for applying a phase correction to one of said two beams being caused to interfere with each other in order to obtain a beat signal having a phase difference proportional to the angle of rotation produced by said sample, wherein feedback is applied to a phase correction amount so that an output produced by phase-detecting said beat signal becomes a maximum or a minimum, and the angle of rotation is detected from said phase correction amount.

7. A device for measurement of angle of rotation as claimed in claim 6, wherein said phase correcting element is a liquid crystal device.

8. A method for measurement of angle of rotation wherein: a coherent beam is split into two beams, one being an object beam and the other being a reference beam; said object beam, after passage through a sample, is converted by a quarter wave plate into mutually perpendicular polarization components having therebetween a phase difference proportional to the angle of rotation produced by said sample, and is caused to interfere with said reference beam having a slight frequency difference relative to said object beam; and the angle of rotation produced by said sample is measured based on a phase difference occurring between two beat signals resulting from said interference.

9. A device for measurement of angle of rotation, comprising: a coherent light source; a quarter wave plate for converting the angle of rotation produced by a sample into a phase difference between mutually perpendicular polarization components after passage through said sample; frequency modulating means for frequency-modulating one of said polarization components; a polarizer for obtaining an interference signal between said mutually perpendicular polarization components; and optical-to-electrical converting means for converting said interference signal into an electrical signal, wherein said frequency modulating means makes use of a phase modulating means constructed from a liquid crystal device.

10. A device for measurement of angle of rotation, comprising: a coherent light source; a quarter wave plate for converting the angle of rotation produced by a sample into a phase difference between mutually perpendicular polarization components after passage through said sample; frequency modulating means for frequency-modulating one of said polarization components; a polarizer for obtaining an interference signal between said mutually perpendicular polarization components; and optical-to-electrical converting means for converting said interference signal into an electrical signal, a phase correcting element for applying a phase correction to one of said polarization components being caused to interfere with each other in order to obtain a beat signal having a phase difference proportional to the angle of rotation produced by said sample, wherein feedback is applied to a phase correction amount so that an output produced by phase-detecting said beat signal becomes a maximum or a minimum, and the angle of rotation is detected from said phase correction amount.

11. A device for measurement of angle of rotation as claimed in claim 10, wherein said phase correcting element is a liquid crystal device.

12. A device for measurement of angle of rotation as claimed in claim 5, wherein said phase correcting element is a liquid crystal device.

* * * * *